(12) United States Patent
Viswanathan

(10) Patent No.: US 8,369,934 B2
(45) Date of Patent: Feb. 5, 2013

(54) CONTACT OVER-TORQUE WITH THREE-DIMENSIONAL ANATOMICAL DATA

(75) Inventor: Raju R. Viswanathan, St. Louis, MO (US)

(73) Assignee: Stereotaxis, Inc., St. Louis, MO (US)

(*) Notice: Subject to any disclaimer, the term of this patent is extended or adjusted under 35 U.S.C. 154(b) by 104 days.

(21) Appl. No.: 12/830,708

(22) Filed: Jul. 6, 2010

(65) Prior Publication Data

US 2011/0022029 A1 Jan. 27, 2011

Related U.S. Application Data

(62) Division of application No. 11/314,826, filed on Dec. 20, 2005, now Pat. No. 7,751,867.

(60) Provisional application No. 60/637,504, filed on Dec. 20, 2004.

(51) Int. Cl.
*A61B 5/055* (2006.01)
*A61B 19/00* (2006.01)

(52) U.S. Cl. ......... 600/424; 600/407; 600/411; 128/898

(58) Field of Classification Search .................. None
See application file for complete search history.

(56) References Cited

U.S. PATENT DOCUMENTS

| | | | |
|---|---|---|---|
| 5,353,807 A | 10/1994 | DeMarco | |
| 5,654,864 A | 8/1997 | Ritter et al. | |
| 5,707,335 A | 1/1998 | Howard et al. | |
| 5,779,694 A | 7/1998 | Howard et al. | |
| 5,931,818 A | 8/1999 | Werp et al. | |
| 6,014,580 A | 1/2000 | Blume et al. | |
| 6,015,414 A | 1/2000 | Werp et al. | |
| 6,128,174 A | 10/2000 | Ritter et al. | |
| 6,148,823 A | 11/2000 | Hastings | |
| 6,152,933 A | 11/2000 | Werp et al. | |
| 6,157,853 A | 12/2000 | Blume et al. | |
| 6,212,419 B1 | 4/2001 | Blume et al. | |
| 6,241,671 B1 | 6/2001 | Ritter et al. | |
| 6,272,370 B1 | 8/2001 | Gillies et al. | |
| 6,292,678 B1 | 9/2001 | Hall et al. | |
| 6,296,604 B1 | 10/2001 | Garibaldi et al. | |
| 6,298,257 B1 | 10/2001 | Hall et al. | |
| 6,298,259 B1 | 10/2001 | Kucharczyk et al. | |
| 6,304,768 B1 | 10/2001 | Blume et al. | |
| 6,311,082 B1 | 10/2001 | Creighton, IV et al. | |
| 6,315,709 B1 | 11/2001 | Garibaldi et al. | |
| 6,330,467 B1 | 12/2001 | Creighton, IV et al. | |

(Continued)

OTHER PUBLICATIONS

Magnetic Manipulation Instrumentation for Medical Physics Research Authors: G. T. Gillies, r. C. Ritter, W. C. Broaddus, M. S. Grady, M. A. Howard, III, R. G. McNeil 1994 American Institute of Physics Rev. Sci. Instrum. vol. 65, No. 3, Mar. 1994 pp. 533-562.

(Continued)

*Primary Examiner* — Long V. Le
*Assistant Examiner* — Angela M Hoffa
(74) *Attorney, Agent, or Firm* — Harness, Dickey & Pierce, P.L.C.

(57) ABSTRACT

A method is provided for establishing contact of a medical device against a three-dimensional surface geometry within a subject body, the method comprising obtaining a three-dimensional tissue surface geometry of an anatomical region within the subject body, obtaining a target location on the surface for the device to contact, determining local surface geometry information in a neighborhood of the target location, and using this information to determine a change of at least one control variable for effecting an over-torque of the medical device to enhance contact of the device with the target surface.

17 Claims, 1 Drawing Sheet

U.S. PATENT DOCUMENTS

| | | |
|---|---|---|
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 | 6/2002 | Garibaldi et al. |
| 6,428,551 B1 * | 8/2002 | Hall et al. ............... 606/159 |
| 6,459,924 B1 | 10/2002 | Creighton, IV et al. |
| 6,475,223 B1 | 11/2002 | Werp et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,529,761 B2 | 3/2003 | Creighton, IV et al. |
| 6,537,196 B1 | 3/2003 | Creighton, IV et al. |
| 6,542,766 B2 | 4/2003 | Hall et al. |
| 6,562,019 B1 | 5/2003 | Sell |
| 6,630,879 B1 | 10/2003 | Creighton, IV et al. |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,740,103 B2 | 5/2004 | Werp et al. |
| 6,755,816 B2 | 6/2004 | Ritter et al. |
| 6,786,219 B2 | 9/2004 | Garibaldi et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,940,379 B2 | 9/2005 | Creighton |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,017,584 B2 | 3/2006 | Garibaldi et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 7,072,703 B2 | 7/2006 | Zhang et al. |
| 7,137,976 B2 | 11/2006 | Ritter et al. |
| 7,161,453 B2 | 1/2007 | Creighton, IV |
| 7,189,198 B2 | 3/2007 | Harburn et al. |
| 7,190,819 B2 | 3/2007 | Viswanathan |
| 7,211,082 B2 | 5/2007 | Hall et al |
| 7,248,914 B2 | 7/2007 | Hastings et al. |
| 7,264,584 B2 | 9/2007 | Ritter et al. |
| 7,276,044 B2 | 10/2007 | Ferry et al. |
| 7,286,034 B2 | 10/2007 | Creighton |
| 7,305,263 B2 | 12/2007 | Creighton, IV |
| 7,313,429 B2 | 12/2007 | Creighton, IV et al. |
| 7,341,063 B2 | 3/2008 | Garbibaldi et al. |
| 7,346,379 B2 | 3/2008 | Eng et al. |
| 7,389,778 B2 | 6/2008 | Sabo et al. |
| 7,416,335 B2 | 8/2008 | Munger |
| 7,495,537 B2 | 2/2009 | Tunay |
| 7,505,615 B2 | 3/2009 | Viswanathan |
| 7,516,416 B2 | 4/2009 | Viswanathan et al. |
| 7,537,570 B2 | 5/2009 | Kastelein |
| 7,540,288 B2 | 6/2009 | Viswanathan et al. |
| 7,540,866 B2 | 6/2009 | Viswanathan et al. |
| 7,543,239 B2 | 6/2009 | Viswanathan et al. |
| 7,555,331 B2 | 6/2009 | Viswanathan |
| 7,567,233 B2 | 7/2009 | Garibaldi et al. |
| 7,603,905 B2 | 10/2009 | Creighton, IV |
| 7,623,736 B2 | 11/2009 | Viswanathan |
| 7,625,382 B2 | 12/2009 | Werp et al. |
| 7,627,361 B2 | 12/2009 | Viswanathan |
| 7,630,752 B2 | 12/2009 | Viswanathan |
| 7,635,342 B2 | 12/2009 | Ferry et al. |
| 7,657,075 B2 | 2/2010 | Viswanathan |
| 7,662,126 B2 | 2/2010 | Creighton, IV |
| 7,690,619 B2 | 4/2010 | Wolfersberger |
| 7,708,696 B2 | 5/2010 | Ritter et al. |
| 7,742,803 B2 | 6/2010 | Viswanathan et al. |
| 7,747,960 B2 | 6/2010 | Garibaldi et al. |
| 7,751,867 B2 | 7/2010 | Viswanathan |
| 7,756,308 B2 | 7/2010 | Viswanathan |
| 7,757,694 B2 | 7/2010 | Ritter et al. |
| 7,761,133 B2 | 7/2010 | Viswanathan et al. |
| 7,766,856 B2 | 8/2010 | Ferry et al. |
| 7,769,428 B2 | 8/2010 | Viswanathan et al. |
| 7,769,444 B2 | 8/2010 | Pappone |
| 7,771,415 B2 | 8/2010 | Ritter et al. |
| 7,771,437 B2 | 8/2010 | Hogg et al. |
| 7,772,950 B2 | 8/2010 | Tunay |
| 7,774,046 B2 | 8/2010 | Werp et al. |
| 7,815,580 B2 | 10/2010 | Viswanathan |
| 7,818,076 B2 | 10/2010 | Viswanathan |
| 7,961,926 B2 * | 6/2011 | Viswanathan ............... 382/128 |
| 8,027,714 B2 * | 9/2011 | Shachar ................ 600/424 |
| 2001/0038683 A1 | 11/2001 | Ritter et al. |
| 2002/0019644 A1 | 2/2002 | Hastings et al. |
| 2002/0100486 A1 | 8/2002 | Creighton, IV et al. |
| 2002/0177789 A1 * | 11/2002 | Ferry et al. ............... 600/585 |
| 2004/0006301 A1 | 1/2004 | Sell et al. |
| 2004/0019447 A1 | 1/2004 | Shachar |
| 2004/0030244 A1 | 2/2004 | Garibaldi et al. |
| 2004/0064153 A1 | 4/2004 | Creighton, IV et al. |
| 2004/0068173 A1 * | 4/2004 | Viswanathan ............... 600/407 |
| 2004/0096511 A1 * | 5/2004 | Harburn et al. ............... 424/489 |
| 2004/0133130 A1 | 7/2004 | Ferry et al. |
| 2004/0147829 A1 | 7/2004 | Segner et al. |
| 2004/0157082 A1 | 8/2004 | Ritter et al. |
| 2004/0158972 A1 | 8/2004 | Creighton, IV et al. |
| 2004/0186376 A1 | 9/2004 | Hogg et al. |
| 2004/0199074 A1 * | 10/2004 | Ritter et al. ............... 600/424 |
| 2004/0249262 A1 * | 12/2004 | Werp et al. ............... 600/411 |
| 2004/0249263 A1 * | 12/2004 | Creighton, IV ............... 600/411 |
| 2004/0260172 A1 | 12/2004 | Ritter et al. |
| 2004/0267106 A1 | 12/2004 | Segner et al. |
| 2005/0004585 A1 | 1/2005 | Hall et al. |
| 2005/0020911 A1 | 1/2005 | Viswanathan et al. |
| 2005/0021063 A1 | 1/2005 | Hall et al. |
| 2005/0033162 A1 | 2/2005 | Garibaldi et al. |
| 2005/0043611 A1 * | 2/2005 | Sabo et al. ............... 600/411 |
| 2005/0065435 A1 | 3/2005 | Rauch et al. |
| 2005/0096589 A1 | 5/2005 | Shachar |
| 2005/0113628 A1 * | 5/2005 | Creighton et al. ............... 600/1 |
| 2005/0113812 A1 | 5/2005 | Viswanathan et al. |
| 2005/0119556 A1 | 6/2005 | Gillies et al. |
| 2005/0119687 A1 | 6/2005 | Dacey, Jr. et al. |
| 2005/0182315 A1 | 8/2005 | Ritter et al. |
| 2005/0256398 A1 | 11/2005 | Hastings et al. |
| 2005/0273130 A1 | 12/2005 | Sell |
| 2006/0009735 A1 * | 1/2006 | Viswanathan et al. ..... 604/95.01 |
| 2006/0025675 A1 | 2/2006 | Viswanathan et al. |
| 2006/0025679 A1 | 2/2006 | Viswanathan et al. |
| 2006/0025719 A1 | 2/2006 | Viswanathan et al. |
| 2006/0036125 A1 * | 2/2006 | Viswanathan et al. ......... 600/11 |
| 2006/0036163 A1 | 2/2006 | Viswanathan |
| 2006/0036213 A1 | 2/2006 | Viswanathan et al. |
| 2006/0041178 A1 * | 2/2006 | Viswanathan et al. ......... 600/11 |
| 2006/0041179 A1 * | 2/2006 | Viswanathan et al. ......... 600/11 |
| 2006/0041180 A1 * | 2/2006 | Viswanathan et al. ......... 600/11 |
| 2006/0041181 A1 | 2/2006 | Viswanathan et al. |
| 2006/0041245 A1 * | 2/2006 | Ferry et al. ............... 604/510 |
| 2006/0058646 A1 * | 3/2006 | Viswanathan ............... 600/434 |
| 2006/0074297 A1 * | 4/2006 | Viswanathan ............... 600/424 |
| 2006/0079745 A1 * | 4/2006 | Viswanathan ............... 600/407 |
| 2006/0079812 A1 * | 4/2006 | Viswanathan ............... 600/585 |
| 2006/0093193 A1 * | 5/2006 | Viswanathan ............... 382/128 |
| 2006/0094956 A1 | 5/2006 | Viswanathan |
| 2006/0100505 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |
| 2006/0270948 A1 | 11/2006 | Viswanathan et al. |
| 2006/0278248 A1 | 12/2006 | Viswanathan |
| 2007/0016010 A1 | 1/2007 | Creighton, IV et al. |
| 2007/0016131 A1 | 1/2007 | Munger et al. |
| 2007/0021731 A1 | 1/2007 | Garibaldi et al. |
| 2007/0021742 A1 | 1/2007 | Viswanathan |
| 2007/0021744 A1 | 1/2007 | Creighton, IV |
| 2007/0032746 A1 | 2/2007 | Sell |
| 2007/0038065 A1 | 2/2007 | Creighton, IV et al. |

| | | |
|---|---|---|
| 2007/0038074 A1 | 2/2007 | Ritter et al. |
| 2007/0040670 A1 | 2/2007 | Viswanathan |
| 2007/0043455 A1 | 2/2007 | Viswanathan et al. |
| 2007/0049909 A1 | 3/2007 | Munger |
| 2007/0055124 A1 | 3/2007 | Viswanathan et al. |
| 2007/0060829 A1 | 3/2007 | Pappone |
| 2007/0060916 A1 | 3/2007 | Pappone |
| 2007/0060962 A1 | 3/2007 | Pappone |
| 2007/0060992 A1 | 3/2007 | Pappone |
| 2007/0062546 A1 | 3/2007 | Viswanathan et al. |
| 2007/0062547 A1 | 3/2007 | Pappone |
| 2007/0073288 A1 | 3/2007 | Hall et al. |
| 2007/0123964 A1 | 5/2007 | Davies et al. |
| 2007/0146106 A1 | 6/2007 | Creighton, IV |
| 2007/0149946 A1 | 6/2007 | Viswanathan et al. |
| 2007/0161882 A1 | 7/2007 | Pappone |
| 2007/0167720 A1 | 7/2007 | Viswanathan |
| 2007/0179492 A1 | 8/2007 | Pappone |
| 2007/0197899 A1 | 8/2007 | Ritter et al. |
| 2007/0197906 A1 | 8/2007 | Ritter |
| 2007/0225589 A1 | 9/2007 | Viswanathan |
| 2007/0250041 A1 | 10/2007 | Werp |
| 2007/0270686 A1 | 11/2007 | Ritter et al. |
| 2007/0287909 A1* | 12/2007 | Garibaldi et al. ............. 600/424 |
| 2008/0004595 A1 | 1/2008 | Viswanathan |
| 2008/0006280 A1 | 1/2008 | Aliberto et al. |
| 2008/0015427 A1 | 1/2008 | Kastelein et al. |
| 2008/0015670 A1 | 1/2008 | Pappone |
| 2008/0016677 A1 | 1/2008 | Creighton, IV |
| 2008/0016678 A1 | 1/2008 | Creighton, IV et al. |
| 2008/0039705 A1 | 2/2008 | Viswanathan |
| 2008/0039830 A1 | 2/2008 | Munger et al. |
| 2008/0043902 A1 | 2/2008 | Viswanathan |
| 2008/0058608 A1 | 3/2008 | Garibaldi et al. |
| 2008/0058609 A1 | 3/2008 | Garibaldi et al. |
| 2008/0059598 A1 | 3/2008 | Garibaldi et al. |
| 2008/0064933 A1 | 3/2008 | Garibaldi et al. |
| 2008/0065061 A1 | 3/2008 | Viswanathan |
| 2008/0077007 A1 | 3/2008 | Hastings et al. |
| 2008/0092993 A1 | 4/2008 | Creighton, IV |
| 2008/0097200 A1 | 4/2008 | Blume et al. |
| 2008/0114335 A1 | 5/2008 | Flickinger et al. |
| 2008/0132910 A1 | 6/2008 | Pappone |
| 2008/0200913 A1 | 8/2008 | Viswanathan |
| 2008/0208912 A1 | 8/2008 | Garibaldi |
| 2008/0228065 A1 | 9/2008 | Viswanathan et al. |
| 2008/0228068 A1 | 9/2008 | Viswanathan et al. |
| 2008/0287909 A1 | 11/2008 | Viswanathan et al. |
| 2008/0294232 A1 | 11/2008 | Viswanathan |
| 2008/0312673 A1 | 12/2008 | Viswanathan et al. |
| 2008/0319303 A1 | 12/2008 | Sabo et al. |
| 2009/0012821 A1 | 1/2009 | Besson et al. |
| 2009/0062646 A1 | 3/2009 | Creighton et al. |
| 2009/0082722 A1 | 3/2009 | Munger et al. |
| 2009/0105579 A1 | 4/2009 | Garibaldi |
| 2009/0105645 A1 | 4/2009 | Kidd et al. |
| 2009/0131798 A1 | 5/2009 | Minar et al. |
| 2009/0131927 A1 | 5/2009 | Kastelein et al. |
| 2009/0138009 A1 | 5/2009 | Viswanathan et al. |
| 2009/0177032 A1 | 7/2009 | Garibaldi et al. |
| 2009/0177037 A1 | 7/2009 | Viswanathan et al. |
| 2009/0306643 A1 | 12/2009 | Pappone et al. |
| 2010/0063385 A1 | 3/2010 | Garibaldi et al. |
| 2010/0097315 A1 | 4/2010 | Garibaldi et al. |
| 2010/0163061 A1 | 7/2010 | Creighton |
| 2010/0168549 A1 | 7/2010 | Pappone |

OTHER PUBLICATIONS

International Search Report and Written Opinion for corresponding PCT/US/2005/046641 Dated: Sep. 27, 2007 pp. 7.

* cited by examiner

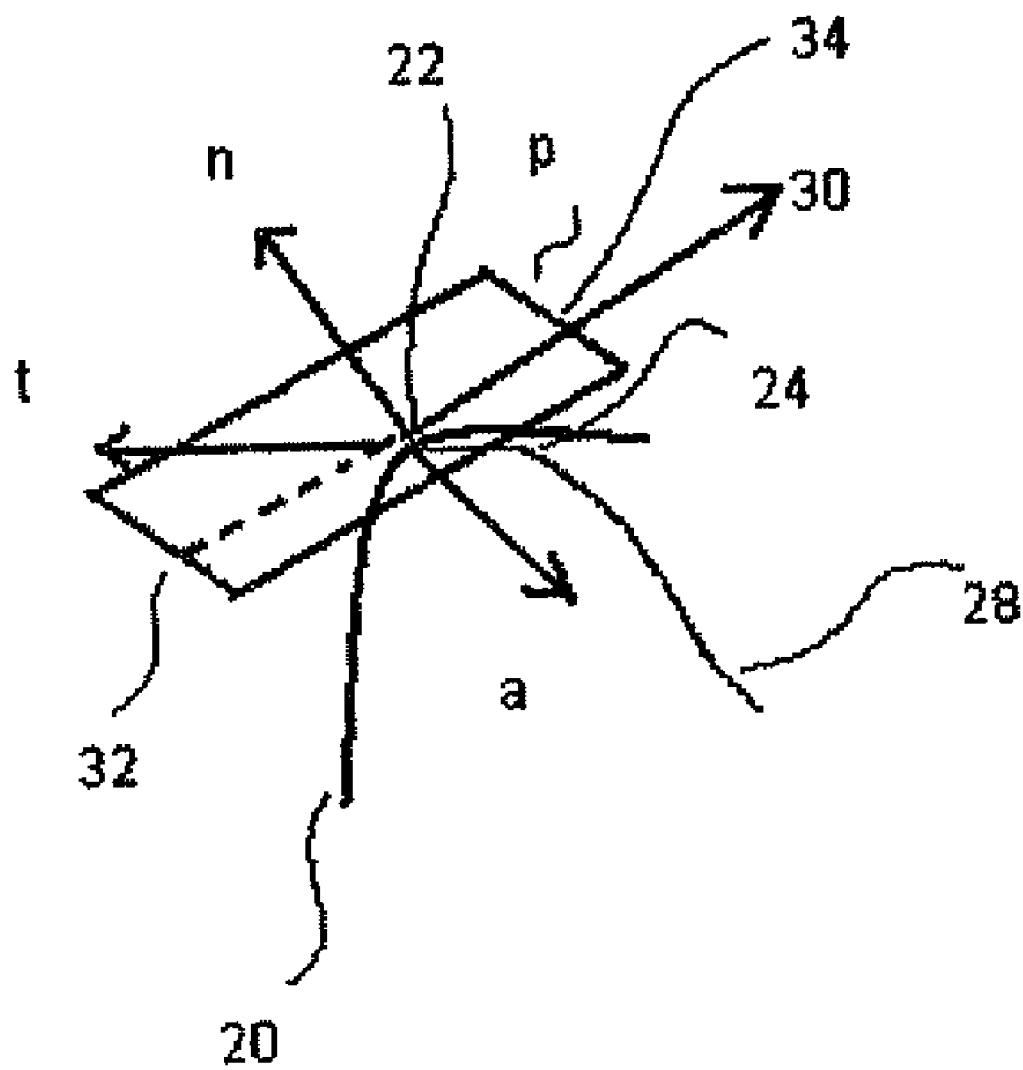

CONTACT OVER-TORQUE WITH THREE-DIMENSIONAL ANATOMICAL DATA

CROSS-REFERENCE TO RELATED APPLICATIONS

This is a divisional application of U.S. patent application Ser. No. 11/314,826, filed Dec. 20, 2005, which is now U.S. Pat. No. 7,751,867, which issued Jul. 6, 2010, which claims priority to U.S. Provisional Patent Application No. 60/637,504, filed Dec. 20, 2004.

FIELD OF THE INVENTION

This invention relates to control of medical devices in a subject body, and more particularly to placement of medical devices in a target location of the subject body.

BACKGROUND OF THE INVENTION

Interventional medicine is the collection of medical procedures in which access to the site of treatment is made through one of the patient's blood vessels, body cavities or lumens. For example, electro-physiology mapping of the heart is most often performed using a catheter which may be inserted into a patient's arterial system through a puncture of the femoral artery in the groin area. Other interventional medical procedures include assessment and treatment of tissues on the inner surfaces of the heart (endocardial surfaces) accessed via peripheral veins or arteries, treatment of vascular defects such as cerebral aneurysms, removal of embolic clots and debris from vessels, treatment of tumors via vascular access, endoscopy of the intestinal tract, etc.

Interventional medicine technologies have been applied to manipulation of instruments which contact tissues during surgical procedures, making these procedures more precise, repeatable and less dependent of the device manipulation skills of the physician. Some presently available interventional medical systems for directing and manipulating the distal tip of a medical device by actuation of the distal portion of the device use computer assisted navigation and an imaging system for providing imaging of the device and blood vessels and tissues. Such systems can control the navigation of a medical device, such as a catheter, to a target destination in an operating region using a computer to orient and guide the distal tip through blood vessels and tissue. In some cases, when the computed direction for reaching the target destination is determined and the medical device is extended, it is desired to establish sufficient contact of the medical device with the intended target location on the three dimensional tissue surface. Adequate contact with the tissue surface within the subject body is important, for instance, in the analysis and treatment of cardiac arrhythmias. A method is therefore desired for controlling movement of a medical device that will establish adequate contact with the target tissue surface and will allow for treatment of the targeted area.

SUMMARY OF THE INVENTION

The method and apparatus of the present invention facilitates the placement of the distal end of a medical device, such as a catheter or microcatheter, against a target location on a three-dimensional curved surface within a subject body. Generally, the present invention comprises a method for establishing contact of a medical device against a three-dimensional surface geometry within a subject body, the method comprising obtaining a three-dimensional tissue surface geometry of a location within the subject body, identifying a desired target location on the surface, computationally determining at least one point spaced from the desired target, stepping a minimum distance from the at least one point to determine whether an image threshold is crossed, and determining a change of at least one control variable for effecting an over-torque of a medical device to enhance contact of the device with the target surface.

In one aspect of the present invention, a three-dimensional surface geometry is suitably rendered in an image model and registered with a known location within the subject body. The model may be used to perform a stepping process to determine if an image surface threshold is crossed, and to determine at least one control variable that may be changed to effect a movement of a virtual or real medical device. The image model of the three-dimensional surface geometry and medical device may be used to predict over-torque of the real or virtual medical device corresponding to the control variable.

In another aspect of the present invention, at least some embodiments of a method provide for determining an over-torque magnetic field to be applied to a medical device to establish adequate contact of the medical device against the target surface of the subject body. In one embodiment, the method allows the user to identify the desired location on an image of the body, which is used to determine an appropriate over-torque rotation corresponding to the local surface geometry at the target location. These and other features and advantages will be in part apparent, and in part pointed out hereinafter.

BRIEF DESCRIPTION OF THE DRAWINGS

FIG. 1 is an illustration of a curved three dimensional tissue surface and a medical device held in contact with the surface through the over-torque method in accordance with the principles of the present invention.

DETAILED DESCRIPTION OF THE INVENTION

In a preferred embodiment of the present invention, a method for establishing contact over-torque of the tip of a medical device against a tissue surface within a subject body is provided in accordance with the principles of the present invention. In one embodiment, the method provides for enhancing contact of a medical device with a tissue surface such as the heart, through the suitable application of an over-torque magnetic field. While this embodiment is operable with magnetically navigable medical devices, other embodiments of a method in accordance with the present invention may be used with medical devices that are guided without magnetic navigation but instead use other control methods for remote navigation such as mechanical actuation, electrostrictive actuation, or hydraulic actuation. The method for establishing contact of a medical device against a surface within a subject body comprises obtaining a three-dimensional tissue surface geometry of a region within the subject body, identifying a desired target location on the surface, defining at least one point spaced from the desired target, computationally stepping a minimum distance from the at least one point to determine whether an image threshold is crossed, and determining a change of at least one control variable for effecting an over-torque of a medical device to enhance contact of the device with the target surface.

A medical device such as a catheter may be navigated to the interior of a subject body of a patient by various means, including but not limited to magnetic navigation. Once the medical device has been navigated to a target surface of the body, such as a heart wall, the contact of the medical device against the tissue may be enhanced by suitably over-torquing the medical device against the tissue surface. A virtual representation of the medical device may be suitably rendered in a three-dimensional model of the surface geometry, and the method may then be used to determine a change to a control variable for affecting an over-torque of the medical device against the surface tissue. Such virtual modeling of the medical device may be used to predict the over-torque of the medical device prior to movement of the actual medical device. Where the medical device is a magnetically navigable medical device, the over-torque may be applied through the application of a magnetic field. Where a magnetically navigable medical device is used, for example, this may be accomplished by applying a magnetic moment in a direction that provides the maximum over torque (i.e., leads the orientation of the catheter tip by an angle of approximately 90° as measured about an axis that is normal to the plane defined by the catheter tip orientation and the local surface normal). This over-torque may be used to enhance contact with the tissue to obtain improved electro-physiology electrical readings, or to apply improved ablation treatment. A suitable over-torque of the magnetic field and the medical device depends on the local surface geometry of the target location within the body. In the following we shall describe the particular case when magnetic field actuation is used to remotely navigate the medical device, as a non-limiting example of an actuation method. Other actuation techniques could be employed as would be familiar to persons skilled in the art of remote surgical navigation.

Referring to FIG. 1, the tissue surface 20 of a three dimensional object in a subject body is represented by curve having a tangential plane p and an outward unit normal vector $\vec{n}$ at a target location point $\vec{x}_0$ (indicated at 22). The local surface geometry of the surface may be obtained from a three-dimensional pre-operative image of the anatomy, or from geometric mapping and anatomical 3D reconstruction that may be performed by reconstructing an interpolated anatomical surface based on endocardial surface locations that have been visited with a catheter device and a localization system that is suitably registered with the computer-controlled navigation system. Since the three-dimensional data of the surface is available, the unit normal vector $\vec{n}$ at the target location may be determined from this data. The tip of a virtual medical device 24, or the tip of the actual medical device where localization data is available, is positioned against the tissue surface 20 near the target location, and a unit tangent vector (device tip orientation) at the tip of the virtual medical device 24 is defined as $\vec{t}$. The unit vector corresponding to the orientation of the medical device base is defined as $\vec{u}$ shown at 28 in FIG. 1. With the medical device positioned against the surface 20, the field vector of the magnetic navigation system is also defined as $\vec{B}_0$. An orthogonal vector $\vec{a}$ is defined as $\vec{a}' = \vec{t} \times \vec{n}$, and suitably normalized $$\vec{a} = \frac{\vec{a}'}{|\vec{a}'|}.$$

Next, a vector $\vec{c}$ (indicated at 30) that is orthogonal to unit normal vector $\vec{n}$ is defined as $\vec{c} = \vec{n} \times \vec{a}$, such that $\vec{a}$ and $\vec{c}$ span the local tangent plane p at point $\vec{x}_0$. Then, two points indicated at 32 and 34 are defined as:

$\vec{x}_1 = \vec{x}_0 - l\vec{c}$, and $\vec{x}_2 = \vec{x}_0 l\vec{c}$, where the distance/is approximately 4 to 7 millimeters.

Next, starting from $\vec{x}_1$, incremental steps in the $-\vec{n}$ direction are made (computationally) at an increment of about 1-5 millimeters. The incremental step is made in association with a three-dimensional image model of the surface geometry, which may determine whether the incremental step results in an image threshold crossing. The above distances are suitable for applications of determining the curvature of certain surfaces such as the interior of a heart. It should be noted that the above distances and increments are exemplary in nature, and may be varied for a variety of applications. If an image intensity threshold crossing of the surface occurs during the stepping process (e.g. the intensity value changes from a low value to a high value), the surface is locally positively curved in the device deflection plane. If no intensity threshold crossing of the surface occurs, the surface is locally negatively curved in approximately the device deflection plane. This can be confirmed by incrementally stepping in the $-\vec{n}$ direction starting from $\vec{x}_2$, to confirm the absence of any image threshold crossings at $\vec{x}_2$.

In one preferred embodiment of the present invention, if there is no occurrence of an image intensity threshold crossing, the vector a (defined above) is redefined and set equal to the vector u defining the base of the medical device: $\vec{a} \leftarrow \vec{u}$. In a second preferred embodiment, the vector c is used to redefine a: a←c. In a third preferred embodiment, the principal directions of curvature of the surface at the target location are determined using the deviation of the shape of a local surface patch away from the local tangent plane as given by standard methods of differential geometry, and the principal direction v corresponding to the minimum signed curvature is used to redefine a: a←v.

As an illustrative non-limiting example of changing a control variable in order to enhance surface contact, we consider the case of magnetic navigation, where an externally applied magnetic field is used to actuate and generally control the configuration of a magnetically endowed medical device. Other actuation technologies could be used for the same purpose and in these other cases the change of control variable would be mapped suitably as could be determined by persons skilled in the art of the appropriate actuation technology with the help of the teachings contained herein.

In the case of magnetic navigation, in general the external magnetic field can be suitably oriented or rotated to optimize surface contact of the medical device with the local tissue surface. In order to determine the rotation of the medical device, the field vector will be rotated about the (rotation axis) vector $\vec{a}$ (suitably defined in various embodiments as described above) by an angle θ to establish a new field vector defined as:

$$\vec{B} = R_{\vec{a}}(\theta)\vec{B}_0 \qquad (1)$$

These methods of the various embodiments generally ensure that the tip of the medical device either directly pushes out against the local tissue surface, or in cases where the surface curvature is not suitably optimal, pushes sideways against the surface in a direction of strongly positive curvature. In either case contact with the local surface position is enhanced and stabilized, which feature is helpful for instance when the tissue surface is in motion, as in the case of the endocardial surface.

If vector $\vec{a}=(a_x, a_y, a_z)$, then a 3×3 skew-symmetric matrix can be defined as:

$$A = \begin{pmatrix} 0 & -a_z & a_y \\ a_z & 0 & -a_x \\ -a_y & a_x & 0 \end{pmatrix} \quad (2)$$

and the rotation matrix for rotating the device about axis a can be written as:

$$R_{\vec{a}}(\theta) = I_{3\times 3} + \sin\theta A + (1-\cos\theta)A^2, \quad (3)$$

where I is the 3×3 identity matrix To determine the angle of rotation θ for the rotation matrix in equation (3), we initially determine the lag angle $\phi = \cos^{-1}(\vec{t}\cdot\vec{B}_0)$. We can use $\theta \approx (\pi/2 - \phi)$ as a reasonable assumption for a good value of θ. The tip of the medical device 24 may then be rotated according to the rotation matrix in equation (3) above. Alternatively, the angle θ can be defined or set by the user using a slider on a Graphical User Interface. The range of the slider could be limited in some embodiments, so that for example the slider range could correspond to rotation angles θ in the range (−30 degrees, 45 degrees) in one preferred embodiment. In alternate embodiments different slider ranges could be used. In one preferred embodiment the rotation angle is applied incrementally based on any rotation that has already been applied so that the total rotation angle measured from the original field configuration (corresponding to the catheter tip just touching the target location) is θ as determined by the slider setting. An example of the latter embodiment is the case when catheter tip localization (position and orientation) information is available. Given the desired angle of rotation that is thus determined, the magnet system is controlled to apply a magnetic field in a direction that provides the requisite over-torque such that catheter tip contact with the tissue surface is enhanced. Once the tip has established firm contact with the surface 20 and is not able to move further, the tip is not aligned with the field vector $\vec{B}_0$. Thus, the lag between the field vector $\vec{B}_0$ and the actual orientation of the tip can provide an indication that the tip of the medical device is in an over-torque contact with the surface 20. Likewise, where an imaging system is used, the prolapse or bend in the distal portion of the medical device 24 that can be seen in the acquired images, or the observation that the device tip has not changed position may also indicate that the tip has established an over-torque contact with the surface 20. The method of determining the rotation of the field vector automatically can also account for the lag angle and other physical properties of the medical device, as given above.

The advantages of the above described embodiment and improvements should be readily apparent to one skilled in the art, as to enabling over-torque of a medical device and thereby enhancing device-tissue contact against a three dimensional surface within a subject body when the device is controlled by a remote navigation system. The actual controls used by the remote navigation system could comprise actuation schemes employing any one or more of magnetic, mechanical, electrostrictive, hydraulic or other actuation means familiar to those skilled in the art. Additional design considerations may be incorporated without departing from the spirit and scope of the invention. Accordingly, it is not intended that the invention be limited by the particular embodiment or form described above, but by the appended claims.

What is claimed is:

1. A method for establishing contact of a magnetically navigable medical device against a three-dimensional target surface geometry within a subject body, the method comprising:
    obtaining a three dimensional geometry of a tissue surface of an anatomical region within a subject body;
    identifying a desired target location on the tissue surface geometry and a local plane tangent to the target location;
    defining at least two points within the local tangent plane which are spaced a predetermined distance from the desired target location;
    incrementally stepping a minimum distance from the at least two points in a direction opposite the outward normal to the tangent plane, to determine whether a surface threshold has been crossed so as to indicate a curvature of a target surface local to the target location;
    using the indicated curvature, determining a rotation of a magnetic field vector for providing an over-torque magnetic field for improving the contact of a medical device with the target surface;
    suitably registering the tissue surface geometry with the subject body; and
    applying the determined rotation of a magnetic field vector to force the medical device against the target surface.

2. The method of claim 1 wherein the crossing of the threshold is determined within a model of the three-dimensional target surface geometry.

3. The method of claim 1 wherein the stepping process is performed for a virtual medical device within a three-dimensional model of the target surface geometry to determine if an image surface threshold is crossed.

4. The method of claim 3 wherein the rotation of a field vector for providing an over-torque magnetic field is utilized to effect a movement of the virtual medical device and to predict the over-torque of the medical device against the target surface.

5. The method of claim 1 wherein the medical device is a localized device and the stepping process is performed for the localized device using a three-dimensional model of the target surface geometry to determine if an image surface threshold is crossed.

6. The method of claim 5 wherein the step of determining whether a threshold has been crossed determines whether the surface has at least one direction of negative curvature.

7. The method of claim 6 wherein the rotation of the magnetic field vector is based on whether the surface has at least one direction of negative curvature.

8. The method of claim 1 wherein the three-dimensional tissue surface geometry is a pre-operative image that is suitably registered with the subject body.

9. The method of claim 1 wherein the three-dimensional tissue surface geometry is obtained from a localization system that maps the local surface geometry.

10. The method of claim 1 wherein the incremental stepping process comprises incrementally moving a minimum distance from the at least two points, and determines whether a threshold has been crossed to discern if the surface is negatively curved or positively curved.

11. The method of claim 10 wherein the at least two points are spaced a predetermined distance from the target, and the two points are within the local tangent plane containing the target location point.

12. The method of claim 11 wherein the predetermined distance is in the range of 4 to 7 millimeters.

13. The method of claim 12 wherein the incremental stepping of a minimum distance is in the range of about 1 to 5 millimeters.

14. The method of claim 1, wherein the applying of a magnetic field comprises a magnetic navigation system applying a magnetic field that leads the orientation of the medical device tip by a pre-determined amount in the same plane as that of the device.

15. The method of claim 1, wherein the applying of a magnetic field comprises a magnetic navigation system applying a magnetic field that leads the orientation of the medical device tip by a user-selected amount in the same plane as that of the device.

16. The method of claim 1 wherein the method further comprises comparing the angular lag between the magnetic field vector and the actual orientation of the tip of the medical device to determine whether the medical device has established over-torque contact.

17. A method for determining a control variable for establishing over-torque of a medical device against a three-dimensional tissue surface geometry within a subject body, the method comprising:
- obtaining local surface geometry information in an anatomical region of a subject body;
- identifying a desired target location on the surface;
- defining at least one point spaced from the desired target;
- evaluating an image model of the surface at the at least one point for the presence of an image threshold crossing;
- determining a change of at least one control variable, based on the evaluation, for effecting an over-torque of a medical device to improve contact of the device against the surface; and
- configuring a navigation system to effect the over-torque based on the change of the at least one control variable and based on a suitable registration of the surface with the subject body.

* * * * *